United States Patent [19]

de Klein

[11] 4,322,570

[45] Mar. 30, 1982

[54] PROCESS FOR THE ADDITION OF A CHLORINATED METHANE CONTAINING AT LEAST THREE CHLORINE ATOMS TO AN ETHYLENICALLY UNSATURATED HYDROCARBON

[75] Inventor: Willem J. de Klein, Dieren, Netherlands

[73] Assignee: Akzona Incorporated, Asheville, N.C.

[21] Appl. No.: 777,370

[22] Filed: Mar. 14, 1977

Related U.S. Application Data

[63] Continuation of Ser. No. 627,410, Oct. 30, 1975, abandoned.

[30] Foreign Application Priority Data

Nov. 4, 1974 [NL] Netherlands ............... 7414329

[51] Int. Cl.$^3$ .............................................. C07C 17/28
[52] U.S. Cl. ................................................. 570/257
[58] Field of Search ................... 260/658 C; 570/257

[56] References Cited

U.S. PATENT DOCUMENTS 2,440,800  5/1948  Hanford et al. ................. 260/658
2,833,808  5/1958  Brendlein ..................... 260/658 X
3,213,149  10/1965  Takahashi et al. ............... 260/658
3,462,503  8/1969  Rieve ........................... 260/658
3,471,579  10/1969  Kubicek ....................... 260/658 X

FOREIGN PATENT DOCUMENTS 2548625  5/1976  Fed. Rep. of Germany ... 260/658 C

OTHER PUBLICATIONS

Gould, "Inorganic Reactions and Structure", pp. 406–408, (1955).

*Primary Examiner*—Delbert E. Gantz
*Assistant Examiner*—Joseph A. Boska
*Attorney, Agent, or Firm*—Francis W. Young; Robert F. Green

[57] ABSTRACT

An addition product of a chlorinated methane containing at least 3 chlorine atoms and an ethylenically unsaturated hydrocarbon is prepared by heating at about 70° to about 250° C. in the presence of a manganese compound in which the manganese has a valence of at least 3 as a radical initiator, and a compound containing a carbonyl group the free ligands of which compounds are at either side linked to a carbon atom, such as an aliphatic ketone.

13 Claims, No Drawings

4,322,570

PROCESS FOR THE ADDITION OF A CHLORINATED METHANE CONTAINING AT LEAST THREE CHLORINE ATOMS TO AN ETHYLENICALLY UNSATURATED HYDROCARBON

This is a continuation of application Ser. No. 627,410, filed Oct. 30, 1975, now abandoned.

BACKGROUND OF THE INVENTION

The invention relates to a process for the addition of a chlorinated methane containing at least three chlorine atoms to an ethylenically unsaturated hydrocarbon in the presence of a radical initiator.

The aforementioned process results in the formation of a halogenated aliphatic hydrocarbon, and is described generally in U.S. Pat. No. 2,440,800. While the process is one of addition, it is promoted by the presence of a radical initiator organic peroxide, such as benzoyl peroxide, which may lead to a limited degree of polymerization. Under these conditions, the process may involve the concurrent formation of telomers. By the term telomer there is to be understood a limited polymerization product of at least two molecules of an ethylenically unsaturated hydrocarbon, to which product one molecule of a methane containing at least three chlorine atoms has been coupled.

With the use of the lower olefins, such as ethylene and propylene in the reaction, the formation of telomer is generally desirable, but in the case of the higher olefins containing more than 6 carbon atoms, this is generally not the case.

The known process, such as that of U.S. Pat. No. 2,440,800, has the disadvantage that peroxides, and particularly organic peroxides, are used as radical initiators. These have the disadvantage that they are very sensitive to explosive decomposition. Moreover, the decomposition products released upon the use of these peroxides are generally difficult to remove from the reaction mixture and practically do not lend themselves for regeneration. Organic peroxides consequently constitute an important cost factor in the preparation of chemical products the synthesis of which takes place under the influence of radicals.

For these reasons there has been proposed in French Pat. No. 1,375,705 the use of an inorganic peroxide, namely nickel peroxide, which can be regenerated and is easy to remove from the reaction mixture by filtration. The disadvantages attendant upon use of this peroxide, however, include its high price, the large amounts to be used, and especially the long reaction times. Another considerable disadvantage to nickel peroxide is that relatively little monomer addition product and a large proportion of telomers are formed.

GENERAL DESCRIPTION OF THE INVENTION

In accordance with the present invention there is provided a novel process for the addition of a chlorinated methane containing at least three chlorine atoms to an ethylenically unsaturated hydrocarbon, to produce the addition product, while at the same time, depending upon the conditions chosen, to control the formation of telomers, so as to yield desirable amounts of telomers if desired.

In performing the addition reaction, in accordance with the invention, there is employed as a radical initiator, a manganese compound in which the manganese has a valence of at least three. Simultaneously there is employed in the reaction mixture a compound containing a carbonyl group, the free ligands of which compounds are at either side linked to a carbon atom.

The preparation in this manner of the addition product of one mole of a chlorinated methane containing at least three chlorine atoms to one mole of an ethylenically unsaturated hydrocarbon will result in a yield of more than 85%. Calculated on the basis of, for trivalent manganese added, the yield may be even more than 2000%.

An important advantage of the process according to the invention is that the divalent manganese compound formed during the reaction can easily be regenerated. Another important advantage of the process according to the invention is that the reaction can readily be carried out explosion-free, even in the absence of a diluent, such as, for example, iso-octane. The use of a diluent in turn involves the risk of formation of additional by-products because of the reaction with it of the radicals contained in the reaction mixture.

It should be noted that the possible use of a manganese salt as catalyst in a process of the type described above is mentioned in U.S. Pat. No. 3,213,149. The manganese salt, however, is mentioned along with salts of metals such as lithium, potassium, sodium, magnesium, and calcium, which, in the absence of the alkanolamines used in all the examples of the patent do not lead to any yield at all. Even after a long reaction time the yield is of hardly any significance. Moreover, the presence of amines, which are generally known to be sensitive to oxidation, are not conducive to the use of a metal salt of which the metal has a relatively high valence, as would be the case with a manganese compound in which the manganese has a valence of at least three.

It is also known from Netherlands patent specification No. 6,908,612 that the use of an at least trivalent manganese compound leads to addition of carbonyl group-containing compounds with an α—H atom to ethylenically unsaturated hydrocarbon compounds. This means that in the light of prior art the use of the present process would rather be expected to lead to an addition of the compound containing the carbonyl group to the unsaturated hydrocarbon.

Surprisingly, however, virtually only addition of the chlorinated methane takes place, and hardly any of the carbonyl compound is consumed at all.

The chlorinated methane containing at least three chlorine atoms is exemplified by chloroform $CHCl_3$, and carbon tetrachloride $CCl_4$.

The term ethylenically unsaturated hydrocarbon as employed herein includes both a cyclic and an acyclic, substituted or unsubstituted hydrocarbon having one or more C=C linkages which do not form an aromatic ring system, nor are connected to such a system. As examples of suitable acyclic hydrocarbons there are mentioned; olefin hydrocarbons containing from 2 to 24 carbon atoms, such as, ethylene, propylene, 1-butylene, 2-butylene, 3-methyl-1-butylene, 1-hexylene, 1-octylene, 1,dodecylene, 2-dodecylene, 1-hexadecylene and 1-octadecylene. Examples of cyclic hydrocarbons include: cyclohexylene, cyclo-octylene.

Additional examples of acyclic hydrocarbons are those containing two double bonds, such as 1,3-butadiene and 1,5-hexadiene.

The foregoing hydrocarbons may be substituted, examples of substituents being: halogen, such as chlorine or bromine; cyano, alkoxy or methylenealkoxy, acetoxy or methyleneacetoxy, and aryl, such as phenyl, for example the compound allylbenzene. Also suitable as addition compounds in the process of the invention are the unsaturated fatty acids, such as oleic acid, linolenic acid, and the like.

In accordance with the invention, it has been found that the addition reaction proceeds best when carried out in the presence of a trivalent manganese compound, such as a trivalent manganese salt. The manganic salt may be derived from either an inorganic acid or an organic acid. The inorganic salt may be, for example manganic sulfate $Mn_2(SO_4)_3$ or manganic phosphate. The organic acid salts are preferably those derived from an aliphatic carboxylic acid containing from 2 to 18 carbon atoms, which may be saturated or unsaturated. Suitable trivalent manganese salts include the acetate, propionate, butyrate, valerate, caprate, caprylate, laurate, stearate, and oleate.

It has further been found that the reaction proceeds best and meets with a minimum of technological problems if there is employed, as the aforesaid carbonyl containing compound, an aliphatic ketone containing from 3 to 10 carbon atoms. The ketones may be derived from straight-chain or branched chain alkyl groups, and may, if desired, carry substituents, such as a carboxyl group or a halogen atom. Examples of suitable ketones include acetone, methyl ethyl ketone, methyl isobutyl ketone, di-isobutyl ketone, and methyl octyl ketone. Acetone is preferred because it is relatively inexpensive and easy to isolate from the reaction mixture by distillation.

In principle any trivalent manganic salt is suitable for use in the process of the invention. It is preferred to use a salt of an organic acid of low molecular weight in order to facilitate removal from the reaction mixture. However, higher aliphatic carboxylic acids, such as stearic acid may be used as manganic salts. These acids may also contain substituents, such as halogen or carbonyl groups, for example α-ketoglutaric acid. For economic and technical reasons, the preferred manganic salt is manganic acetate.

The concentration of the manganese compound may vary within wide limits. Favorable results are obtained in a range of 0.001 to 1 mole/l. If use is made of a trivalent manganese salt, the best results are found obtained at concentrations up to 0.1 mole/l. A considerably higher manganese concentration may be attended with the formation of many by-products, in that the formed radicals will interreact or further oxidize. In some cases it may therefore be advisable for the manganese compound to be introduced into the reaction mixture gradually.

The amount in which the compound containing the carbonyl group is to be used also varies within wide limits. The most favorable results are obtained with amounts in the range of about 5 to about 40 percent by volume, calculated on the total volume of chlorinated methane and ethylenically unsaturated hydrocarbon. For technological reasons it may in some cases be advantageous to choose a composition such that an azeotropic mixture is obtained.

As the process according to the invention is effected by a radical mechanism, it will be clear that the concentration ratio of the components of the reaction mixture is of great importance for the proportions of the main products and the by-products finally formed.

The formation of telomer is usually not desirable in the case of the addition of a chlorinated methane to an olefin containing more than six carbon atoms. The invention therefore provides a process in which the molar ratio of chlorinated methane to the ethylenically unsaturated hydrocarbon is at least 10 to 1, and may range up to about 15 to 1.

On the other hand, if telomer formation is desired, which is the case especially if ethylene and propylene are used as the ethylenically unsaturated hydrocarbons, then the concentration of the latter should be chosen higher. If use is made of ethylene and propylene, the reaction will always be carried out in an autoclave, under elevated pressure, and telomer formation will increase with increasing partial pressure of the alkylene used.

In this connection, it is pointed out, however, that the use of a mixture of ethylene and chlorinated methane in the presence of a radical initiator according to the invention is attended with the risk of explosion for example in the case of a relatively high initial concentration of ethylene.

To avoid telomerization it may in some cases be recommended that the ethylenically unsaturated hydrocarbon be added to the reaction mixture gradually.

The temperature at which the process of the invention is carried out is in the range of about 70° to about 250° C., depending upon the reaction components used. Preferrably the temperature is in the range of 80° to 150° C.

The reaction products prepared by the process according to the invention form valuable intermediate products. Thus, heating with concentrated sulfuric acid will cause the trichloromethyl to be hydrolyzed to a carboxyl group. The products obtained by the process of the invention are polychlorinated compounds, particularly polychlorinated aliphatic hydrocarbons, for example 1,1,1-trichloro-3-chlorononane. They are useful as high boiling solvents for waxes, hydrocarbons, and the like, and as fireproofing compounds.

DESCRIPTION OF THE PREFERRED EMBODIMENTS

The following examples illustrate the practice of the invention, but are not to be considered as limiting the invention thereto:

EXAMPLE I

A 2-liter autoclave provided with a stirrer was charged with 100 ml of acetone and 900 ml of carbon tetrachloride and flushed with nitrogen. To these substances were added 4.6 g (0.02 moles) of Mn (III) acetate and 22.4 g (0.2 moles) of n-octylene.

The resulting mixture was kept at 120° C. for 75 minutes. After cooling, filtration of the solid substituents, and distilling off of excess carbon tetrachloride and acetone, there remained 52.9 g of liquid residue containing 85.5% by weight of 1,1,1-trichloro-3-chlorononane. This means that the percentage addition product was 850%, calculated on the total amount of Mn (III) acetate added.

EXAMPLES II-IV

Proceeding as in Example I, the autoclave of Example I was charged with 900 ml of carbon tetrachloride ($CCl_4$), 100 ml of acetone, 4.6 g (0.02 moles) of Mn (III) acetate, and ethylene was used as the ethylenically unsaturated hydrocarbon. The temperature, pressure (at 20° C.) and reaction time were varied as follows:

| Example | Temperature °C. | Ethylene pressure at 20° C. | Atm. 120° C. | Reaction Time (min.) | Residue (g) |
|---|---|---|---|---|---|
| II | 119–135 | 6 | 14 | 75 | 337.0 |
| III | 119–123 | 30 | 66 | 120 | 295.8 |
| IV | 80–120 | 50 | 210 | 120 | 410.3 |

The residue of Example IV (410.3 g) had the following composition:
 33.5 g monomer
 198.5 g dimer
 110 g trimer
 41.5 g tetramer
 22.8 g pentamer

EXAMPLE V

The experiment of Example I was repeated, except that methyl ethyl ketone was used instead of acetone. After cooling, filtration and distillation, there remained 56.75 g of liquid residue which contained 81.4% by weight of 1,1,1-trichloro-3-chlorononane. This means that the percentage addition product was 865%, calculated on the total amount of Mn (III) acetate added.

EXAMPLE VI

The experiment of Example I was repeated, except that methyl isobutyl ketone was used instead of acetone. After cooling, filtration and distillation there remained 62.3 g of liquid product, which contained 75.6% by weight of 1,1,1-trichloro-3-chlorononane. This means that the percentage addition product was 885%, calculated on the total amount of Mn (III) acetate added.

EXAMPLE VII

The autoclave used in the preceeding examples was charged with 100 ml acetone and 900 ml of chloroform, followed by flushing with nitrogen. The contents of the autoclave were then heated to 130° C. A mixture of 20 ml of acetone, 180 ml of chloroform, and 22.4 ml of n-octylene was subsequently divided into 5 equal portions of 44.4 ml each, after which there was added to each portion 1.00 g of finely powdered manganese (III) acetate. The portions were then added one by one to the mixture of acetone and chloroform present in the autoclave. After each addition the temperature was kept at 130° C. for 30 minutes. After successive cooling, release of pressure and filtration the volatile constituents were evaporated. There remained 21.5 g of residue, which upon analysis was found to contain 40% by weight of addition product of chloroform to n-octylene, viz. 1,1,1-trichlorononane. This means that the percentage addition product was 143%, calculated on the total amount of Mn (III) acetate (=0.022 moles) added.

What is claimed is:

1. A process for the preparation of an addition product of a chlorinated methane containing at least 3 chlorine atoms and an ethylenically unsaturated hydrocarbon at a temperature in the range of about 70° to about 250° C. in the presence of a radical initiator comprising a manganese compound in which the manganese has a valence of at least 3, and a compound containing a carbonyl group the free ligands of which compound are at either side linked to a carbon atom, said carbonyl-containing compound also containing an α-hydrogen atom.

2. The process of claim 1 in which the molar ratio of chlorinated methane to ethylenically unsaturated hydrocarbon is at least 10 to 1.

3. The process of claim 1 in which the ethylenically unsaturated hydrocarbon is an olefin hydrocarbon containing from 2 to 24 carbon atoms.

4. The process of claim 1 in which the compound containing a carbonyl group is an aliphatic ketone containing from 3 to 10 carbon atoms.

5. The process of claim 4 in which the ketone is acetone.

6. The process of claim 1 in which the manganese compound is a trivalent manganese salt.

7. The process of claim 6 in which the manganese salt is manganic acetate.

8. The process of claim 1 in which the proportion of the compound containing a carbonyl group is about 5% to about 40% by volume, calculated on the total volume of chlorinated methane and ethylenically unsaturated hydrocarbon.

9. The process of claim 1 in which the ethylenically unsaturated hydrocarbon is incorporated into the reaction mixture gradually.

10. The process of claim 1 in which the manganese compound is incorporated into the reaction mixture gradually.

11. The process of claim 1 in which the chlorinated methane is chloroform.

12. The process of claim 1 in which the chlorinated methane is carbon tetrachloride.

13. The process of claim 1 in which the ethylenically unsaturated hydrocarbon is ethylene.

* * * * *